(12) United States Patent
Ohtake et al.

(10) Patent No.: US 7,497,829 B2
(45) Date of Patent: Mar. 3, 2009

(54) DATA RECORDING SYSTEM

(75) Inventors: Akifumi Ohtake, Mitaka (JP);
Kazufumi Tanaka, Mitaka (JP)

(73) Assignee: Aloka Co., Ltd., Tokyo (JP)

( * ) Notice: Subject to any disclaimer, the term of this patent is extended or adjusted under 35 U.S.C. 154(b) by 467 days.

(21) Appl. No.: 10/965,038

(22) Filed: Oct. 14, 2004

(65) Prior Publication Data

US 2005/0124893 A1 Jun. 9, 2005

(30) Foreign Application Priority Data

Oct. 17, 2003 (JP) .............................. 2003-357813
Oct. 17, 2003 (JP) .............................. 2003-357816

(51) Int. Cl.
*A61B 8/00* (2006.01)
*G01D 9/00* (2006.01)

(52) U.S. Cl. .................................... 600/450; 346/33 B (58) Field of Classification Search ................ 600/450, 600/443, 427, 437, 481; 346/33 ME, 33 B
See application file for complete search history.

(56) References Cited

U.S. PATENT DOCUMENTS

| | | | | |
|---|---|---|---|---|
| 5,443,489 A * | 8/1995 | Ben-Haim | .................. | 607/115 |
| 5,813,986 A * | 9/1998 | Ubukata | .................. | 600/440 |
| 5,843,130 A * | 12/1998 | Jazayeri | .................. | 607/5 |
| 5,865,832 A * | 2/1999 | Knopp et al. | .................. | 606/10 |
| 6,217,515 B1 | 4/2001 | Yamakawa et al. | | |
| 6,352,507 B1 * | 3/2002 | Torp et al. | .................. | 600/438 |
| 6,436,043 B2 * | 8/2002 | Bonnefous | .................. | 600/438 |
| 6,491,636 B2 * | 12/2002 | Chenal et al. | .................. | 600/450 |
| 6,508,769 B2 * | 1/2003 | Bonnefous | .................. | 600/447 |
| 6,572,547 B2 * | 6/2003 | Miller et al. | .................. | 600/437 |
| 6,716,166 B2 * | 4/2004 | Govari | .................. | 600/437 |
| 6,976,961 B2 * | 12/2005 | Jackson et al. | .............. | 600/443 |
| 6,979,294 B1 * | 12/2005 | Selzer et al. | ................ | 600/450 |

FOREIGN PATENT DOCUMENTS

| | | |
|---|---|---|
| JP | 5-184578 | 7/1983 |
| JP | 64-056041 | 3/1989 |
| JP | 6-078306 | 3/1994 |
| JP | 3-97451 | 4/1994 |
| JP | 6-269455 | 9/1994 |
| JP | 8-066399 | 3/1996 |
| JP | 8-163484 | 6/1996 |

(Continued)

*Primary Examiner*—Eric F Winakur
*Assistant Examiner*—Michael T Rozanski
(74) *Attorney, Agent, or Firm*—William L. Androlia; H. Henry Koda (57) ABSTRACT

A ring buffer records image data output from an ultrasound diagnosis device in units of frames. A user identifies, on an image, occurrence of a target symptom while viewing a cross sectional image which is displayed in real time and inputs an end trigger immediately after the symptom occurs. When the end trigger is input, a system controller unit instructs a recording controller unit for recording of image data. The recording controller unit sets a recording start time from the time when the end trigger is input and extracts data corresponding to a period from the recording start time to the time when the end trigger is input from the ring buffer as data to be recorded. A data process is applied to the data to be recorded in a data processor unit and recorded on a recording medium.

15 Claims, 6 Drawing Sheets

FOREIGN PATENT DOCUMENTS

| | | |
|---|---|---|
| JP | 9-116872 | 5/1997 |
| JP | 9-308633 | 12/1997 |
| JP | 10-127631 | 5/1998 |
| JP | 10-314166 | 12/1998 |
| JP | 2000-014668 | 1/2000 |
| JP | 2000-229081 | 8/2000 |
| JP | 2001-095801 | 4/2001 |
| JP | 2001-269335 | 10/2001 |
| JP | 2001-276072 | 10/2001 |
| JP | 2002-065667 | 3/2002 |

* cited by examiner

DATA RECORDING SYSTEM

BACKGROUND OF THE INVENTION

1. Field of the Invention

The present invention relates to a data recording system and in particular to a data recording system which extracts recording data from data obtained through transmission and reception of ultrasound.

2. Description of the Related Art

An apparatus is known in which image data obtained through transmission and reception of ultrasound is recorded and the recorded image data is replayed in a loop (repeatedly replayed). For example, Japanese Patent Laid-Open Publication No. Hei 6-269455 discloses an apparatus which uses an R wave of an electrocardiographic waveforms to send image data of heart beats from a certain time phase of an electrocardiographic R wave to another time phase of the electrocardiographic R wave to an external storage device and record in the external storage device.

In order to record image data for replaying in a loop (loop replay), it is necessary to set a starting point and an ending point of image data such that a target symptom is contained. In the apparatus of Japanese Patent Laid-Open Publication No. Hei 6-269455, an ultrasound image corresponding to image data which is temporarily stored is displayed on a screen and time phases of a starting point and an ending point of image data for which recording is desired are designated on an electrocardiographic waveform also displayed on the screen. In the apparatus of Japanese Patent Laid-Open Publication No. Hei 6-269455, however, operations for extracting data to be recorded are complex as the apparatus requires operations such as, for example, display of an electrocardiographic waveform and setting of both the starting point and the ending point on the electrocardiographic waveform.

In addition, when the image data obtained by an ultrasound diagnosis apparatus is to be recorded in a storage device external to the ultrasound diagnosis apparatus, a recording operation with respect to the external storage device is further required.

SUMMARY OF THE INVENTION

The present invention advantageously provides a data recording system in which data containing a target symptom obtained by an ultrasound diagnosis apparatus can be easily extracted and recorded.

According to one aspect of the present invention, there is provided a data recording system comprising a memory which temporarily stores data obtained from a received signal which is obtained through transmission and reception of ultrasound, and a recording controller unit which extracts recording data from data stored in the memory, wherein the recording controller unit sets a recording start time based on a recording end time designated by a user and extracts data corresponding to a period from the recording start time to the recording end time as the recording data.

With this structure, a recording start time is set based on a recording end time designated by a user and data to be recorded corresponding to a period from the recording start time to the recording end time is extracted. Because of this, it is possible for the user to, for example, easily extract data containing a target symptom by identifying occurrence of the target symptom while viewing an ultrasound image which is displayed in real time and designating the recording end time.

According to another aspect of the present invention, it is preferable that, in the data recording system, the recording start time is a time which is a preset period prior to the recording end time. As the preset period, it is possible to use, for example, a period which is set to a predetermined length by a user such as a number of heart beats and a time value. According to another aspect of the present invention, it is preferable that, in the data recording system, data to be stored in the memory contains electrocardiographic waveform information of a heart which is a target tissue and the recording controller unit sets the recording start time to be a time which is a period designated by the user prior to the recording end time based on the electrocardiographic waveform information. According to another aspect of the present invention, it is preferable that, in the data recording system, data to be stored in the memory contains acquisition time information of a received signal corresponding to the data, and the recording controller unit sets the recording start time to be a time which is a period designated by the user prior to the recording end time using the acquisition time information.

According to another aspect of the present invention, there is provided an ultrasound diagnosis apparatus comprising a memory which temporarily stores data obtained from a received signal which is obtained through transmission and reception of ultrasound, and a controller which extracts recording data to be recorded to a data recording unit from data stored in the memory, wherein the controller sets a recording start time based on a recording end time designated by a user and extracts data corresponding to a period from the recording start time to the recording end time as the recording data.

As described, according to the present invention, it is possible to easily extract and record data containing a target symptom, obtained using an ultrasound diagnosis apparatus.

BRIEF DESCRIPTION OF THE DRAWINGS

A preferred embodiment of the present invention will be described in detail based on the following figures, wherein.

DESCRIPTION OF PREFERRED EMBODIMENT

A preferred embodiment (hereinafter referred to simply as "embodiment") of the present invention will now be described.

Figure 1:
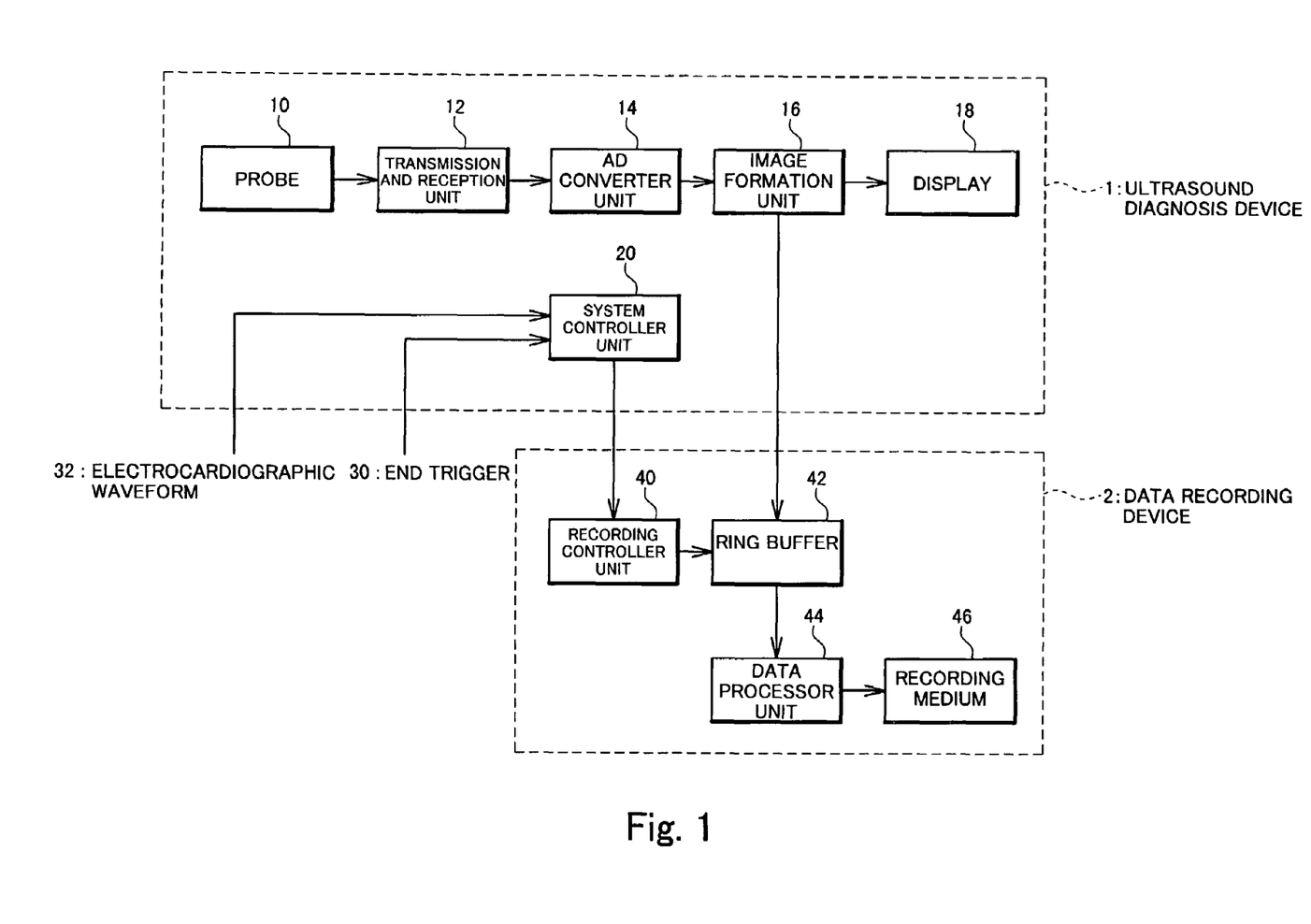
FIG. 1 is a block diagram showing an overall structure of a data recording system according to a preferred embodiment of the present invention.

FIG. 1 is a block diagram showing an overall structure of a data recording system according to a preferred embodiment of the present invention. The data recording system shown on FIG. 1 comprises an ultrasound diagnosis device 1 and a data recording device 2.

A probe 10 transmits and receives ultrasound to and from a space containing a heart which is a target tissue. A transmission and reception unit 12 controls the probe 10 to generate a transmission beam and forms a scan plane across the heart by steering-controlling the transmission beam. The scan plane is formed for each time phase and the transmission and reception unit 12 generates a received beam based on a result of reception by the probe 10 obtained for each time phase and obtains a received signal for each received beam. In general, the scan plane for each time phase is referred to as a "frame" and a plurality of received beams forming each scan surface is referred to as "lines". That is, the transmission and reception unit 12 obtains a received signal for each line in units of frames.

An AD converter unit 14 applies an analog-to-digital conversion (AD conversion) process to the received signal (analog signal) for each line supplied from the transmission and reception unit 12 and outputs the AD converted received data to an image formation unit 16. The image formation unit 16 generates, from the received data, image data corresponding to each fame. The image data is, for example, data of a cross sectional image of a heart. The image data is sequentially generated for each time phase and output to a display 18 which displays an ultrasound image. The image data generated in the image formation unit 16 is also output to a ring buffer 42 of the data recording device 2.

A system controller unit 20 outputs electrocardiographic waveform information and acquisition time information of received data to the data recording device 2 as additional information for the image data. The electrocardiographic waveform information is waveform information obtained from an electrocardiographic waveform 32 of a heart. An end trigger 30 which is input to the system controller unit 20 is a trigger input by a user and a recording operation of data is executed based on the end trigger 30. The recording operation of data will be described later in more detail referring to FIG. 3.

The ring buffer 42 is a memory for recording image data output from the ultrasound diagnosis device 1 in units of frames. Information related to the frame is attached to the image data for each frame.

Figure 2:
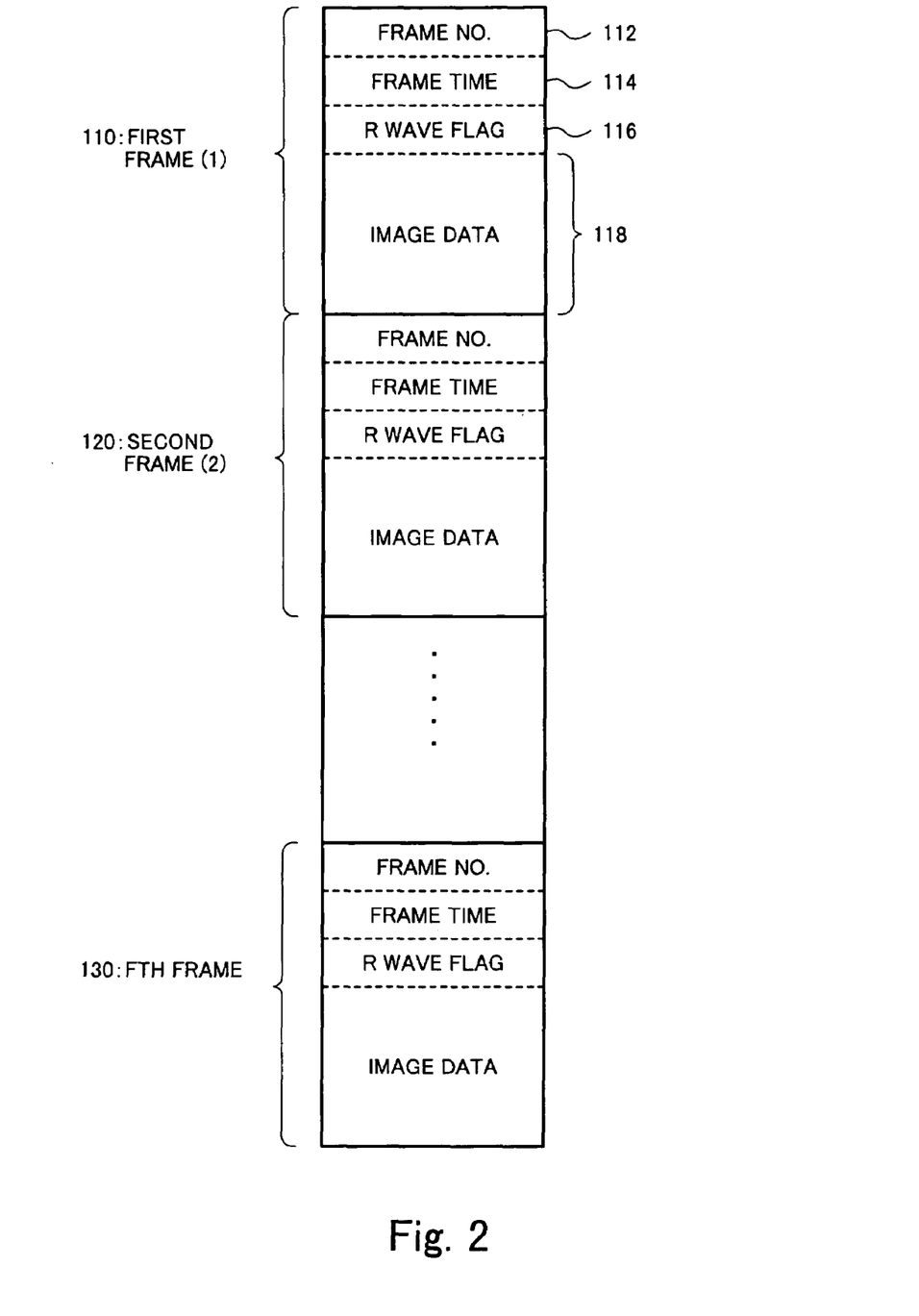
FIG. 2 is a diagram showing a recorded content of a ring buffer of FIG. 1.

FIG. 2 is a diagram showing a recorded content of the ring buffer (reference numeral 42 of FIG. 1). The recorded content of the ring buffer 42 will now be described referring to FIG. 2. Structures shown in FIG. 1 will be explained using the same reference numerals as those in FIG. 1. The ring buffer 42 records, in a time sequential manner from the first address of the ring buffer 42, image data in order of a first frame 110, a second frame 120, . . . and an Fth frame 130 in units of frames. The recorded content in each frame will now be described.

A frame number (frame No.) 112 represents an identification number of the frame. For example, natural numbers from 1 are assigned in order of acquisition of the frames. A frame time 114 indicates the time when the frame is obtained, and acquisition time data generated in the recording controller unit 40 based on acquisition time information supplied from the system controller unit 20 of the ultrasound diagnosis device 1 is recorded in the frame time 114. An R wave flag 116 is a flag indicating presence or absence of detection of an R wave during when the frame is obtained. The R wave is a wave which is observed in an electrocardiographic waveform 32 at the point of telediastolic of a heart. In other words, the recording controller unit 40 detects a timing of the R wave from the electrocardiographic waveform information supplied from the system controller unit 20 and sets the R wave flag 116 to "1" for a frame which is obtained at the timing of the R wave and the R wave flag 116 to "0" for a frame obtained at a timing other than the R wave. Related information such as the frame number (frame No.) 112, frame time 114, and R wave flag 116 are attached to the image data 118 forming each frame and stored in the ring buffer 42.

Image data corresponding to each frame are sequentially recorded in a time sequential manner to the ring buffer 42. When the ring buffer 42 is filled with image data from the first frame to the Fth frame, the recording controller unit 40 overwrites a region to which the image data of the first frame is recorded with the image data of the (F+1)th frame obtained in a time phase following the time phase of the Fth frame. In other words, the image data of the first frame is discarded and image data of the (F+1)th frame is newly recorded. Similarly, when the image data of (F+2)th frame, (F+3)th frame, etc. are obtained, the regions to which the image data of the second frame, the third frame, etc. are recorded are overwritten. In this manner, the ring buffer 42 stores image data and related information thereof for the past F frames from the most recent diagnosis time.

Referring again to FIG. 1, the recording controller unit 40 extracts, from the image data recorded in the ring buffer 42, image data to be recorded and supplies the extracted data to a data processor unit 44. The data processor unit 44 subjects the image data to a data process for recording. When an optical disk recorder is used as the data recording device 2, for example, the data processor unit 44 executes a process to convert the image data to an image format for the optical disk recorder. The data processed image data is recorded on a recording medium 46. When the data recording device 2 is an optical disk recorder, the recording medium 46 corresponds to an optical disk. The data recording device 2 is not limited to an optical disk recorder and may alternatively be, for example, a hard disk recorder, a VTR, and a magnetic disk recorder.

Figure 3:
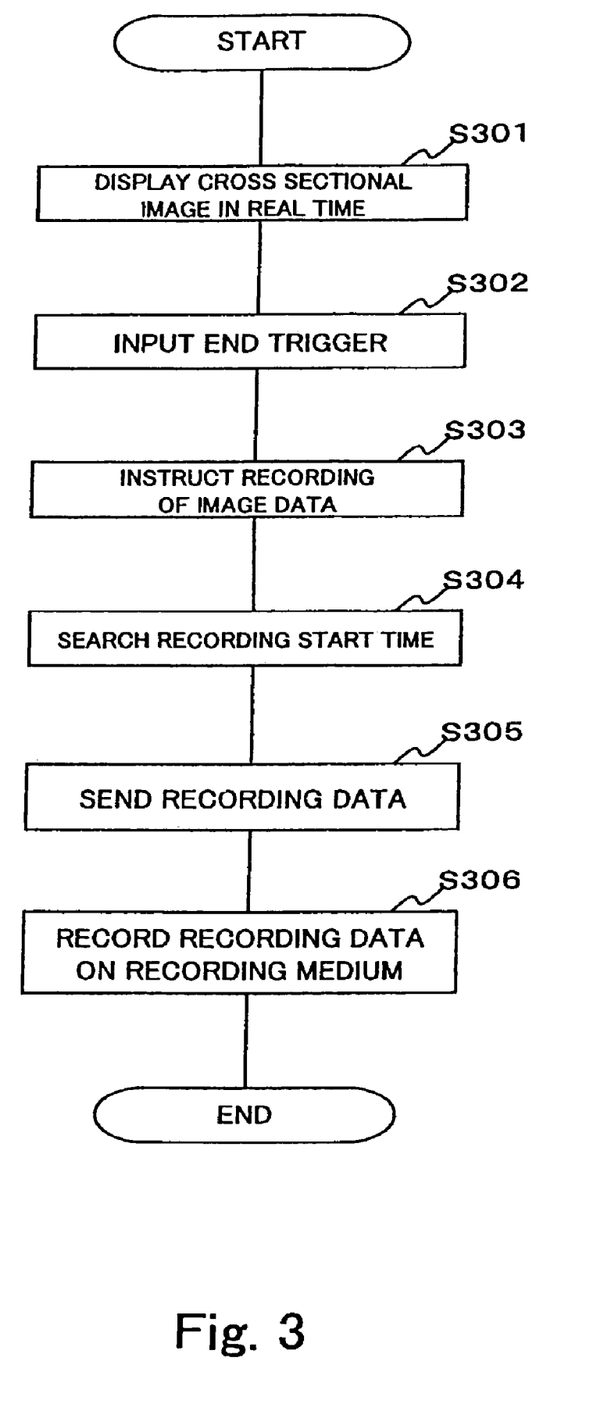
FIG. 3 is a diagram for explaining a recording operation of image data.

FIG. 3 is a diagram for explaining an image data recording operation by the data recording system shown on FIG. 1. The recording operation of the image data will now be described referring to FIG. 3. In the following description, the structures described with reference to FIG. 1 will be explained referring to the same reference numerals as those in FIG. 1.

First, a user operates the probe 10 and allows display of an ultrasound image of a diagnosis target part such as, for example, a cross sectional image of a heart, on the display 18. The image formation unit 16 sequentially generates image data for each frame and the cross sectional image of the heart is displayed on the display 18 in real time (step S301). During this process, the image data generated in the image formation unit 16 is also output to the ring buffer 42.

Next, while viewing the cross sectional image displayed in real time, the user identifies the occurrence of a target symptom of diagnosis on the image, and inputs an end trigger 30 from the operation panel of the ultrasound diagnosis device 1 immediately after the occurrence of the symptom (step S302). Immediately after the user inputs the end trigger 30, the system controller unit 20 instructs the recording controller unit 40 to record image data (step S303).

When the recording controller unit 40 receives the recording instruction of image data, the recording controller unit 40 searches for data of a recording start time from among the data recorded in the ring buffer 42 (step S304). The recording start time is searched based on a setting value which is input by the user in advance. As the setting value, it is preferable to use a count number of the R waves or a time value. For example, when the count number of R waves is set to "3", the recording controller unit 40 searches, from among the data recorded in the ring buffer 42, for data of a frame corresponding to the time of input of the end trigger 30, and then searches for frames having the R wave flag (reference numeral 116 of FIG. 2) of "1" in the past data from the data of the frame corresponding to the end trigger 30 and detects a third frame in the past frames with the R wave flag of "1" as the frame of the recording start time.

Alternatively, when, for example, a time value of "10 seconds" is set by the user, the recording controller unit 40 searches, from among the data recorded in the ring buffer 42, for data of a frame corresponding to the time of input of the end trigger 30 and detects a frame corresponding to a time which is 10 seconds before the time of input of the end trigger 30 as the frame of the recording start time, referring to the frame time (reference numeral 114 of FIG. 2).

When the recording start time is identified, the recording controller unit 40 sends the image data of frames corresponding to a period from the recording start time until the end trigger input time from the ring buffer 42 to the data processor unit 44 as data for recording (step S305). The data processor unit 44 applies a data process corresponding to the recording medium 46 to the sent data for recording and the data to be recorded to which the data process is applied is recorded on the recording medium 46 (step S306).

In this manner, with the data recording system of the present embodiment, the user can identify occurrence, on an image, of a target symptom of diagnosis while viewing cross sectional images which are displayed in real time and store the data for recording containing the symptom on a recording medium 46 by inputting the end trigger 30.

Alternatively, it is also possible to employ a configuration in which the count number of R waves or the time value which is used in the search of the recording start time in step S304 of FIG. 3 can be suitably changed by the user while the user views the real time images and based on a frequency of occurrence of the target symptom, etc. In addition, it is also possible to employ a configuration in which the image data of all frames recorded in the ring buffer 42 are replayed after the end trigger 30 is input and the user then sets the recording start time from which recording to the recording medium 46 is to be started while the user views the replayed images.

The above-described embodiment is described for exemplifying purposes only and should not be construed as limiting the present invention. For example, in the embodiment exemplified in FIG. 1, the image data generated in the image formation unit 16 is output to the ring buffer 42, but it is also possible to employ a configuration in which received data to which an image generation process is not yet applied is output to the ring buffer 42. In this configuration, the received data for each frame is recorded in place of the image data 118 shown in FIG. 2 and data to be recorded extracted from the received data is recorded on the recording medium 46.

In addition, in the above-described embodiment, the recording data to be recorded to the recording medium 46 is extracted by the data recording device, but it is also possible to employ a configuration in which the ultrasound diagnosis device extracts the recording data.

Figure 4:
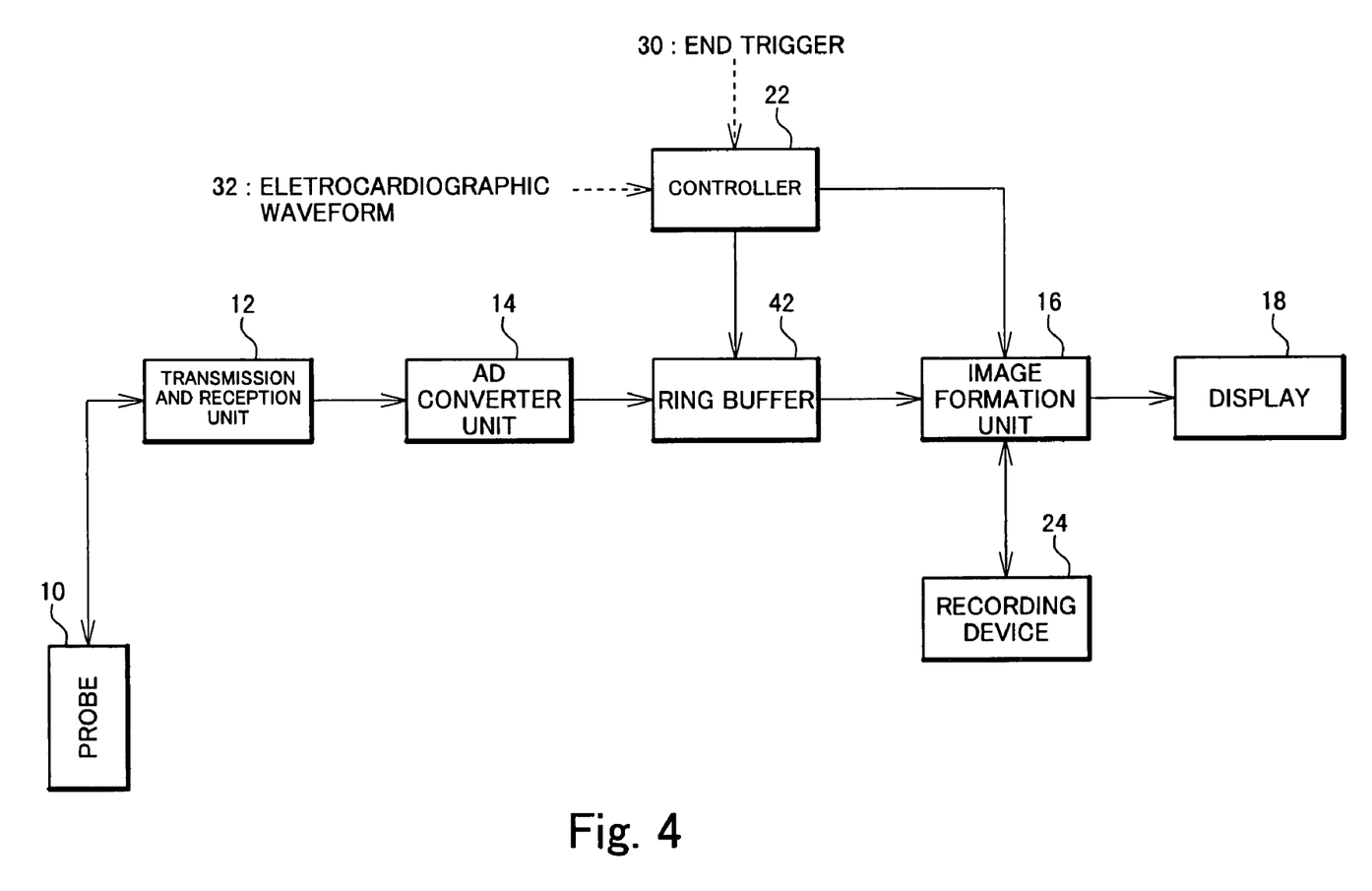
FIG. 4 is a block diagram showing an overall structure of an ultrasound diagnosis apparatus according to a preferred embodiment of the present invention.

FIG. 4 is a block diagram showing an overall structure of an ultrasound diagnosis apparatus according to a preferred embodiment of the present invention.

A probe 10 transmits and receives ultrasound to and from a space containing a heart which is a target tissue. A transmission and reception unit 12 controls the probe 10 to generate a transmission beam and forms a scan plane across the heart by steering-controlling the transmission beam. The scan plane is formed for each time phase and the transmission and reception unit 12 generates a received beam based on a result of reception by the probe 10 obtained for each time phase and obtains a received signal for each received beam. In general, the scan plane for each time phase is referred to as a "frame" and a plurality of received beams forming each scan plane is referred to as "lines". That is, the transmission and reception unit 12 obtains the received signal for each line in units of frames.

An AD converter unit 14 applies an analog-to-digital conversion (AD conversion) process to the received signal (analog signal) for each line supplied from the transmission and reception unit 12 and outputs the AD converted received data to a ring buffer 42. The ring buffer 42 is a memory for recording the received data for each line in units of frames. Information related to the frame is attached to the received data for each frame and the received data is recorded in the ring buffer 42. The content to be recorded to the ring buffer 42 will be described later in more detail referring to FIG. 5.

An image formation unit 16 obtains the received data from the ring buffer 42 according to an instruction by a controller 22. The controller 22 sets an image display mode of the ultrasound diagnosis apparatus to a real time mode or to the loop replay mode according to an operation by the user. In the real time mode, the image formation unit 16 obtains received data corresponding to the most recent frame recorded on the ring buffer 42 and generates image data corresponding to each frame from the obtained received data. Here, the image data is, for example, image data of a cross sectional image of the heart. The image data is sequentially generated for each time phase and displayed on a display 18 as a real time ultrasound image.

On the other hand, in the loop replay mode, the image formation unit 16 generates image data for loop replay using received data corresponding to past frames and recorded in the ring buffer 42. The image data for loop replay is output to the display 18 and to a recording device 24. The display 18 replays and displays the ultrasound image in a loop based on the image data for loop replay and the recoding device 24 stores the image data for loop replay output to the recording device 24. As the recording device 24, it is preferable to use, for example, a VTR, an optical disk recorder, a hard disk recorder, etc. The recording device 24 may be provided within the ultrasound diagnosis apparatus or may be provided externally to the ultrasound diagnosis apparatus. The image data recorded in the recording device 24 is read from the image formation unit 16 as necessary and is displayed on the display 18 as a loop replay image. An image data recording operation to the recording device 24 will be described in more detail later referring to FIG. 6.

The image formation unit 16 may alternatively be configured to directly obtain the received data from the AD converter unit 14 in real time mode and obtain received data corresponding to the past frames recorded in the ring buffer 42 in the loop replay mode.

Figure 5:
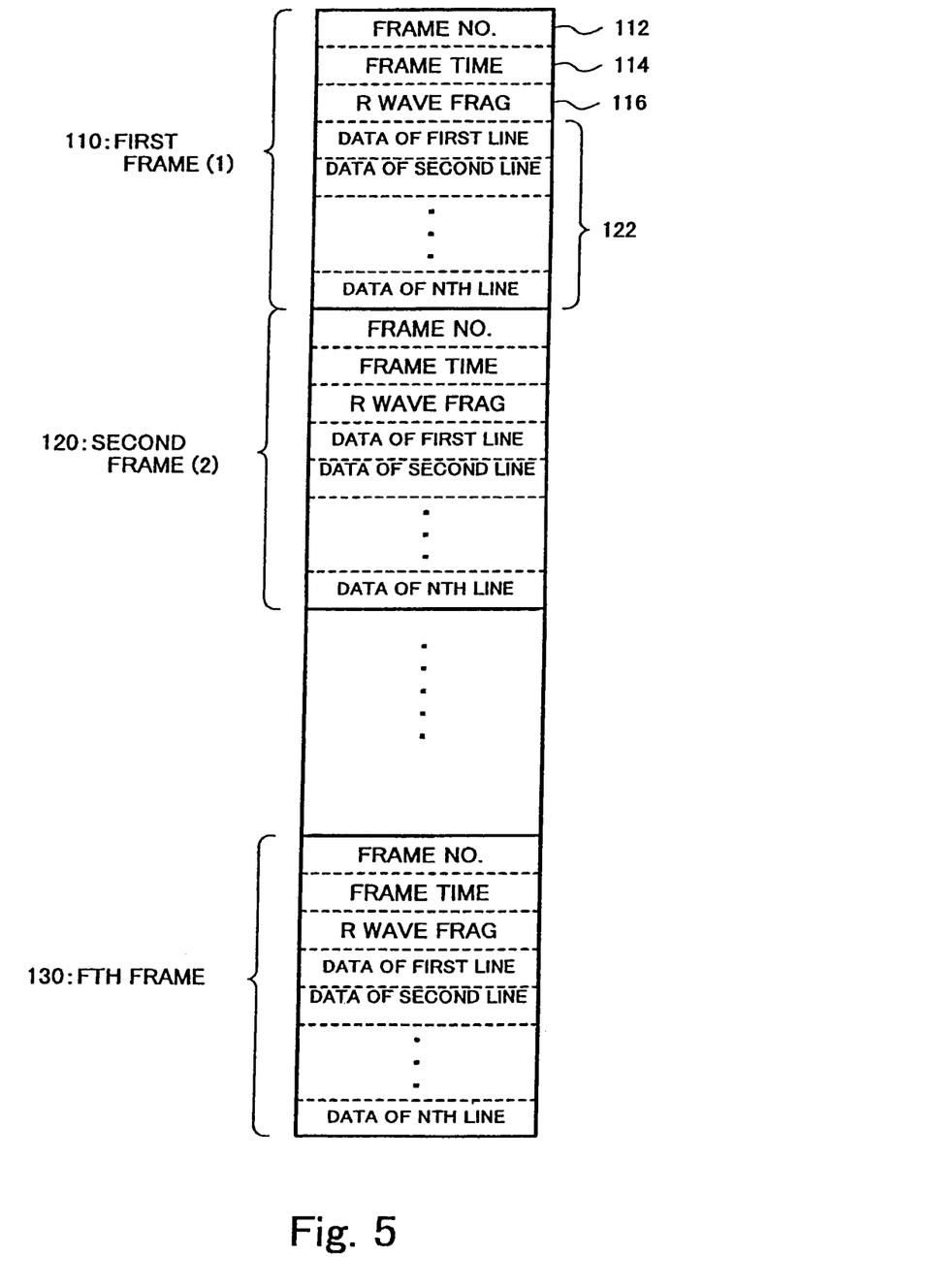
FIG. 5 is a diagram showing a recorded content of the ring buffer of FIG. 4.

FIG. 5 is a diagram showing a recorded content of the ring buffer (reference numeral 42 of FIG. 4). The recorded content of the ring buffer 42 will now be described referring to FIG. 5. Structures shown in FIG. 4 will be explained using the same reference numerals as those in FIG. 4.

The ring buffer 42 records, in a time sequential manner from the first address of the ring buffer 42, data in order of a first frame 110, a second frame 120, . . . and an Fth frame 130 in units of frames. The recorded content for each frame will now be described.

A frame number (frame No.) 112 represents an identification number of the frame. For example, natural numbers from 1 are assigned in order of acquisition of the frames. A frame time 114 indicates the time when the frame is obtained and is recorded based on time data supplied form the controller 22. An R wave flag 116 is a flag indicating presence or absence of detection of an R wave during when the frame is obtained. The R wave is a wave which is observed in an electrocardiographic waveform 32 at the point of telediastolic of a heart. The electrocardiographic waveform 32 is input to the controller 22. The controller 22 detects a timing of the R wave from the electrocardiographic waveform 32 and sets the R wave flag 116 to "1" for a frame which is obtained at the timing of the R wave and the R wave flag to "0" for a frame which is obtained at a timing other than the R wave. The frame number (frame No.) 112, frame time 114, and R wave flag 116 as described are attached to and recorded with line data (received data) 122 from a first line to an Nth line forming each frame.

Received data corresponding to each frame are sequentially recorded in a time sequential manner to the ring buffer 42. When the ring buffer 42 is filled with received data from the first frame to the Fth frame, the controller 22 overwrites a region to which the received data of the first frame is recorded with the received data of the (F+1)th frame obtained in a time phase following the time phase of the Fth frame. In other words, the received data of the first frame is discarded and received data of (F+1)th frame is newly recorded. Similarly, when received data of (F+2)th frame, (F+3)th frame, etc. are obtained, the regions to which the received data of the second frame, third frame, etc. are recorded are overwritten. In this manner, the ring buffer 42 stores received data for the past F frames from the most recent diagnosis time.

The received data stored in the ring buffer 42 is output to the image formation unit 16 according to the replay mode. Specifically, in the real time mode, the received data of the most recent frame stored in the ring buffer 42 is output to the image formation unit 16 and, in the loop replay mode, data for loop replay containing received data corresponding to the past frames is output to the image formation unit 16. The user can identify a symptom which is a target of diagnosis while viewing an ultrasound image such as, for example, a cross sectional image of a heart, which is displayed in real time and easily record the data for loop replay containing the target symptom of diagnosis to the recording device 24. This recording operation will now be described.

Figure 6:
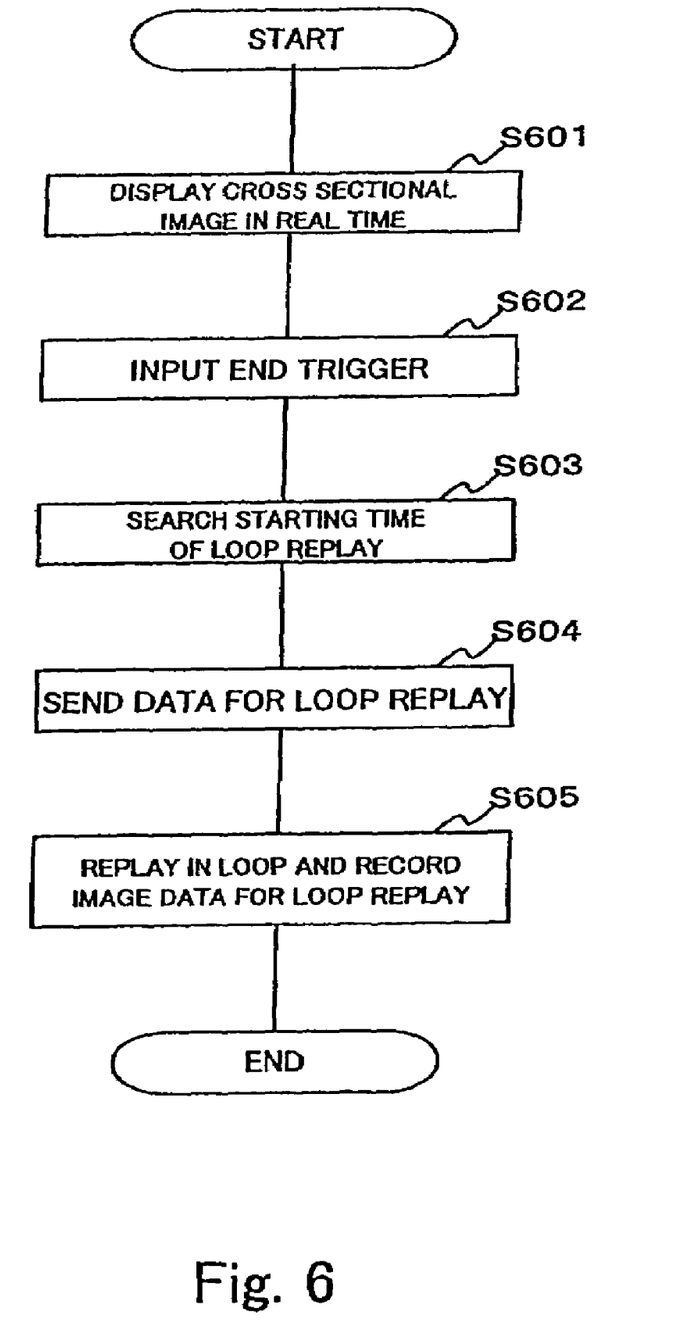
FIG. 6 is a diagram for explaining a recording operation of image data for loop replay.

FIG. 6 is a diagram for explaining a recording operation of image data for loop replay in the ultrasound diagnosis apparatus shown in FIG. 4. The recording operation of the image data for loop replay will now be described referring to FIG. 6. The structures described above with reference to FIG. 4 will be explained using the same reference numerals as those in FIG. 4.

First, a user operates the probe 10 to allow display of an ultrasound image of a diagnosis target part such as, for example, a cross sectional image of the heart, on the display 18. During this process, the ultrasound diagnosis apparatus is set to the real time mode. The image formation unit 16 generates image data based on the received data of the most recent frame and a cross sectional image of the heart is displayed on the display 18 in real time (step S601). Next, the user identifies, on the image, occurrence of a target symptom of diagnosis while viewing the cross sectional image which is displayed in real time and inputs an end trigger 30 from the operation panel immediately after the symptom occurs (step S602) When the user inputs the end trigger 30, the mode of the ultrasound diagnosis apparatus is changed from the real time mode to the loop replay mode. For the replay in loop replay mode, data of past frames recorded in the ring buffer 42 are used. In other words, data from a certain time in the past recorded in the ring buffer 42 till the time when the end trigger 30 is input are extracted. For this purpose, when the end trigger 30 is input, the controller 22 searches for data of the starting time of the loop replay from among the data recorded in the ring buffer 42 (step S603).

The starting time of loop replay is searched based on a setting value which is input by the user in advance. As the setting value, it is preferable to use a count number of the R waves or a time value. For example, when the count number of R waves is set to "3", the controller 22 searches, from among the data recorded in the ring buffer 42, for data of a frame corresponding to the time of input of the end trigger 30, and then searches for frames having the R wave flag (reference numeral 116 of FIG. 5) of "1" in the past data from the data of the frame corresponding to the end trigger 30 and detects a third frame in the past frames with the R wave flag of "1" as the frame of the starting time of loop replay.

Alternatively, when, for example, a time value of "10 seconds" is set as the setting value, the controller 22 searches, from among the data recorded in the ring buffer 42, for data of a frame corresponding to the time of input of the end trigger 30 and detects a frame corresponding to a time which is 10 seconds before the time of input of the end trigger 30 as the frame of the starting time of loop replay, referring to the frame time (reference numeral 114 of FIG. 5).

When the starting time of loop replay is found, the controller 22 sends the data of frames from the starting time of loop replay till the input time of the end trigger from the ring buffer 42 to the image formation unit 16 as the data for loop replay (step S604). The image formation unit 16 generates image data from the sent data for loop replay, allows an image to be displayed on the display 18, and also outputs the generated image data to the recording device 24 to record the data as the image data for loop replay (step S605).

As described, with the ultrasound diagnosis apparatus of the present embodiment, the user can identify the occurrence of a target symptom of diagnosis on an image while viewing a cross sectional image which is displayed in real time and input the end trigger 30, to allow the display 18 to display, in loop, images containing the symptom and record the image data for loop replay.

Alternatively, it is also possible to employ a configuration in which the count number of R waves or the time value which is used in the search of the starting time of loop replay in step S603 of FIG. 6 can be suitably changed by the user while the user views the real time images and based on a frequency of occurrence of the target symptom, etc. In addition, it is also possible to employ a configuration in which all of the frames recorded in the ring buffer 42 are replayed and the user then sets the starting time of loop replay to be recorded to the recording device 24.

The above-described embodiment is described for exemplifying purposes only and should not be construed as limiting the present invention. For example, in the embodiment exemplified in FIG. 4, the data for loop replay extracted from the ring buffer 42 is processed in the image formation unit 16 to the image data for replay and recorded in the recording device 24, but it is also possible to directly record the data for loop replay extracted from the ring buffer 42 to the recording device 24.

In addition, it is also possible to employ a configuration in which the ring buffer 42 provided upstream of the image formation unit 16 is provided downstream of the image formation unit 16. In this configuration, image data generated by the image formation unit 16 is recorded in place of the line data 122 shown in FIG. 5. Also, in this configuration, the controller 22 sends the image data corresponding to the time from the starting time of loop replay until the time when the end trigger is input to the recording device 24 and to the display 18 as the data for loop replay.

Moreover, it is also possible to employ a configuration in which a VTR which is an external device is used as the recording device 24 and the controller 22 supplies a recording instruction through a receiver unit of a remote controller of the VTR. In this configuration, an image signal generated in the image formation unit 16 is supplied to an image input terminal of the VTR. Alternatively, it is also possible to use a hard disk recorder or an optical disk recorder as the recording device 24 and to apply the control for the recording operation by the controller 22 through a dedicated control line such as RS232C interface.

What is claimed is:

1. A data recording system comprising:
   a memory which temporarily stores image data of a plurality of frames obtained from a received signal which is obtained through transmission and reception of ultrasound; and
   a recording controller unit which is configured to set a recording start time based on a recording end time designated by a user and extracts recording data from the image data of the plurality of frames stored in the memory, wherein
   the image data of the plurality of frames stored in the memory has an R wave flag, assigned to each frame, indicating a presence or absence of a detected R wave at a time when the frame is obtained as electrocardiographic waveform information of a heart which is a target tissue,
   wherein the recording controller unit further is configured to set, based on the R wave flag, the recording start time to a time which is a predetermined count number of R waves prior to the recording end time and extracts image data corresponding to a period from the recording start time to the recording end time as the recording data.

2. A data recording system according to claim 1, further comprising:
   an ultrasound diagnosis device, and
   a data recording device, wherein
   the ultrasound diagnosis device comprises an ultrasound probe which transmits and receives ultrasound to and from a space containing a target tissue, and a transmission and reception unit which controls the ultrasound probe to obtain the received signal, and
   the data recording device comprises the memory and the recording controller unit.

3. A data recording system according to claim 2, wherein image data to be stored in the memory contains image data of an ultrasound image output from the ultrasound diagnosis device.

4. A data recording system according to claim 1, wherein the recording controller unit extracts the image data of the plurality of frames corresponding to the period from the recording start time until the recording end time as the recording data by searching, from among the image data of the plurality of frames stored in the memory, for image data of a frame corresponding to the recording end time, and by searching, from among past frames prior to the searched image data, for a frame having the R wave flag indicating the presence of a detected R wave, and further by searching image data of a frame corresponding to the recording start time which is set to a predetermined count number of R waves prior to the recording end time.

5. A data recording system according to claim 4, wherein the image data of the plurality of frames stored in the memory includes time data, assigned to each frame, indicating the time when the frame was obtained; and
   the recording controller unit sets, based on the fine data, the recording start time to a time which is a predetermined time value prior to the recording end time and extracts image data corresponding to the period from the recording start time until the recording end time as the recording data.

6. A data recording system according to claim 5, wherein the recording controller unit extracts image data of the plurality of frames corresponding to the period from the recording start time until the recording end time as the recording data by searching, from among the image data of the plurality of frames stored in the memory, for image data of a frame corresponding to the recording end time, and by searching based on the time data of the searched image, from among past frames prior to the searched image data, for image data of a frame corresponding to the recording start time which is set to a predetermined time value prior to the recording end time.

7. An ultrasound diagnosis apparatus, comprising:
   a memory which temporarily stores data of a plurality of frames obtained from a received signal which is obtained through transmission and reception of ultrasound, and
   a controller which is configured to set a recording start time based on a recording end time designated by a user and extracts recording data to be recorded to a data recording unit from the data of the plurality of frames stored in the memory, wherein
   the data of the plurality of frames stored in the memory has an R wave flag, assigned to each frame, indicating the presence or absence of a detected R wave at a time when the frame is obtained as electrocardiographic waveform information of a heart which is target tissue, and
   wherein the controller further is configured to set, based on the R wave flag, the recording start time to a time which is a predetermined count number of R waves prior to the recording end time and extracts data corresponding to a period from the recording start time to the recording end time as the recording data.

8. An ultrasound diagnosis apparatus according to claim 7, wherein
   the controller extracts data of frames corresponding to the period from the recording start time until the recording end time as the recording data by searching, from among the data of the plurality of frames stored in the memory, for data of a frame corresponding to the recording end time, and by searching, from among past frames prior to the searched data, for a frame having the R wave flag indicating the presence of a detected R wave, and further by searching data of a frame corresponding to the recording start time which is set to a predetermined count number of R waves prior to the recording end time.

9. An ultrasound diagnosis apparatus according to claim 8, wherein
   an image generation process is applied to the recording data in an image formation unit provided downstream of the memory and the processed recording data is recorded in the data recording unit.

10. An ultrasound diagnosis apparatus according to claim 8, wherein
    the memory stores image data to which an image generation process is applied in an image formation unit provided upstream of the memory.

11. An ultrasound diagnosis apparatus according to claim 7, further comprising:
    an ultrasound probe which transmits and receives ultrasound to and from a space containing a target tissue, and a transmission and reception unit which controls the ultrasound probe to obtain the received signal.

12. An ultrasound diagnosis apparatus comprising:
an ultrasound probe which transmits and receives ultrasound to and from a space containing a heart;
a transmission and reception unit which controls the ultrasound probe to obtain a received signal;
a memory which temporarily stores received data of a plurality of frames which is obtained from the received signal;
a controller which is configured to set a recording end time to be a time when a user inputs an end trigger and a recording start time to be a time which is a period designated by the user prior to the recording end time, and extracts received data corresponding to a period from the recording start time to the recording end time from the memory; and
an image formation unit which applies an image generation process to received data extracted from the memory to generate image data and outputs the image data to a data recording unit, wherein
the received data of the plurality of frames stored in the memory has an R wave flag, assigned to each frame, indicating a presence or absence of a detected R wave at a time when the frame is obtained as electrocardiographic waveform information of the heart, and
the controller further is configured to set, based on the R wave flag, the recording start time to a time which is a predetermined count number of R waves prior to the recording end time.

13. An ultrasound diagnosis apparatus according to claim 12, wherein
the controller extracts received data of frames corresponding a period from the recording start time until the recording end time as the recording data by searching, from among the received data of the plurality of frames stored in the memory, for received data of a frame corresponding to the recording end time, and by searching, from among past frames prior to the searched received data, for a frame having the R wave flag indicating the presence of a detected R wave, and further by searching received data of a frame corresponding to the recording start time which is set to a predetermined count number of R waves prior to the recording end time.

14. An ultrasound diagnosis apparatus according to claim 12, wherein
the received data of the plurality of frames stored in the memory includes time data, assigned to each frame, indicating the time when the frame was obtained; and
the controller sets, based on the time data, the recording start time to a time which is a predetermined time value prior to the recording end time.

15. An ultrasound diagnosis apparatus according to claim 12, wherein
the image generation unit outputs the image data to the data recording unit and displays an ultrasound image corresponding to the image data on a display unit.

\* \* \* \* \*